US012763215B2

(12) United States Patent
Mande et al.

(10) Patent No.: US 12,763,215 B2
(45) **Date of Patent: *Oct. 13, 2026**

(54) SYSTEM AND METHOD FOR ASSESSING THE RISK OF SCHIZOPHRENIA

(71) Applicant: Tata Consultancy Services Limited, Mumbai (IN)

(72) Inventors: Sharmila Shekhar Mande, Pune (IN); Tungadri Bose, Pune (IN); Subhrajit Bhar, Pune (IN); Rashmi Singh, Pune (IN); Nishal Kumar Pinna, Pune (IN)

(73) Assignee: TATA CONSULTANCY SERVICES LIMITED, Mumbai (IN)

(*) Notice: Subject to any disclaimer, the term of this patent is extended or adjusted under 35 U.S.C. 154(b) by 1148 days.

This patent is subject to a terminal disclaimer.

(21) Appl. No.: 17/634,634

(22) PCT Filed: Aug. 12, 2020

(86) PCT No.: PCT/IB2020/057573

§ 371 (c)(1),
(2) Date: Feb. 11, 2022

(87) PCT Pub. No.: WO2021/028844

PCT Pub. Date: Feb. 18, 2021

(65) Prior Publication Data

US 2022/0328192 A1 Oct. 13, 2022

(30) Foreign Application Priority Data

Aug. 13, 2019 (IN) ............................ 201921032792

(51) Int. Cl.
*G16H 50/30* (2018.01)
*C12Q 1/6869* (2018.01)
(Continued)

(52) U.S. Cl.
CPC ............ *G16H 50/30* (2018.01); *G16B 25/10* (2019.02); *G16B 30/10* (2019.02); *G16B 40/20* (2019.02); *C12Q 1/6869* (2013.01)

(58) Field of Classification Search
None
See application file for complete search history.

(56) References Cited

U.S. PATENT DOCUMENTS

| | | | | |
|---|---|---|---|---|
| 11,359,249 | B2 * | 6/2022 | Budding | C12Q 1/6883 |
| 2004/0110938 | A1 | 6/2004 | Parekh et al. | |

(Continued)

FOREIGN PATENT DOCUMENTS

| | | | |
|---|---|---|---|
| CA | 2 417 136 | A1 | 3/2002 |
| EP | 1644532 | A2 | 4/2006 |

(Continued)

OTHER PUBLICATIONS

Nguyen, T. T., Kosciolek, T., Maldonado, Y., Daly, R. E., Martin, A. S., McDonald, D., . . . & Jeste, D. V. (2019). Differences in gut microbiome composition between persons with chronic schizophrenia and healthy comparison subjects. Schizophrenia research, 204, 23-29. (Year: 2019).*

(Continued)

*Primary Examiner* — Kaitlyn L Minchella
*Assistant Examiner* — Noah A. Auger
(74) *Attorney, Agent, or Firm* — Finnegan, Henderson, Farabow, Garrett & Dunner, LLP

(57) ABSTRACT

Schizophrenia is a chronic and severe psychiatric disorder that affects how a person thinks, feels, and behaves. If Schizophrenia is diagnosed early, most symptoms of Schizophrenia can be managed with appropriate medical interventions. A system and method for assessing the risk of Schizophrenia in a person has been provided. The system is configured to assess individuals to check the presence or (Continued)

absence of Schizophrenia, by quantifying the abundance of sensory proteins in their microbiome. The method involves assessment and categorization of the person into healthy and schizophrenic based on the abundance of sensory proteins in the microbiome. The systems and methods further describe microbiota based therapeutics for management of Schizophrenia through generating a therapeutic model and administering a consortium of healthy microbes which could modulate the disease microbiome composition towards a healthy equilibrium.

5 Claims, 5 Drawing Sheets

(51) Int. Cl.

| | |
|---|---|
| ***G16B 25/10*** | (2019.01) |
| ***G16B 30/10*** | (2019.01) |
| ***G16B 40/20*** | (2019.01) |

(56) References Cited

U.S. PATENT DOCUMENTS

| | | | | |
|---|---|---|---|---|
| 2019/0292584 | A1* | 9/2019 | Jain | G16B 20/00 |
| 2020/0157609 | A1* | 5/2020 | Bajaj | C12Q 1/6883 |

FOREIGN PATENT DOCUMENTS

| | | | | | |
|---|---|---|---|---|---|
| WO | WO 2007/015113 | A2 | | 2/2007 | |
| WO | WO-2015074054 | A1 | * | 5/2015 | A61K 35/741 |
| WO | WO-2016168316 | A1 | * | 10/2016 | C12Q 1/68 |
| WO | WO 2019/036176 | A1 | | 2/2019 | |

OTHER PUBLICATIONS

Castro-Nallar, E., Bendall, M. L., Pérez-Losada, M., Sabuncyan, S., Severance, E. G., Dickerson, F. B., . . . & Crandall, K. A. (2015). Composition, taxonomy and functional diversity of the oropharynx microbiome in individuals with schizophrenia and controls. PeerJ, 3, e1140. (Year: 2015).*

Yolken, R. H., Severance, E. G., Sabunciyan, S., Gressitt, K. L., Chen, O., Stallings, C., . . . & Dickerson, F. B. (2015). Metagenomic sequencing indicates that the oropharyngeal phageome of individuals with schizophrenia differs from that of controls. Schizophrenia bulletin, 41(5), 1153-1161. (Year: 2015).*

Dinsdale, E. A., Edwards, R. A., Bailey, B. A., Tuba, I., Akhter, S., McNair, K., . . . & Ponomarenko, V. (2013). Multivariate analysis of functional metagenomes. Frontiers in genetics, 4, 41. (Year: 2013).*

Shen, Y., Xu, J., Li, Z., Huang, Y., Yuan, Y., Wang, J., . . . & Liang, Y. (2018). Analysis of gut microbiota diversity and auxiliary diagnosis as a biomarker in patients with schizophrenia: a cross-sectional study. Schizophrenia research, 197, 470-477. (Year: 2018).*

Bradshaw et al., "Aggregation of the Protein TRIOBP-1 and Its Potential Relevance to Schizophrenia," PLoS One, 9(10): e111196 (2014).

International Search Report for PCT/IB2020/057573, dated Mar. 8, 2021, 3 pages.

Kho et al., "The Human Gut Microbiome—A Potential Controller of Wellness and Disease," Front. Microbiol. 9:1835 (2018).

Lee et al., "EyeSite: a semi-automated database of protein families in the eye," Nucleic Acids Research, 32 (2004).

Written Opinion of the International Searching Authority, dated Mar. 8, 2021, 7 pages.

Zhu et al., "Identification of gut microbiome markers for schizophrenia delineates a potential role of *Streptococcus*," (2018).

* cited by examiner

SYSTEM AND METHOD FOR ASSESSING THE RISK OF SCHIZOPHRENIA

PRIORITY CLAIM

This application is an US National Stage Filing and claims priority from International Application No. PCT/IB2020/057573, filed on Aug. 12, 2020, which application claims priority from Indian Provisional Patent Application No. 201921032792, filed on Aug. 13, 2019. The entire contents of the aforementioned application are incorporated herein by reference.

TECHNICAL FIELD

The embodiments herein generally relate to the field of psychiatric disorders, and, more particularly, to a method and system for assessing the risk of Schizophrenia in a person.

BACKGROUND

Schizophrenia is a chronic and severe psychiatric disorder that affects how a person thinks, feels, and behaves. When Schizophrenia is active, symptoms can include delusions, hallucinations, trouble with thinking and concentration, and lack of motivation. Till date, here is no cure for Schizophrenia. However if Schizophrenia is diagnosed early, most symptoms of Schizophrenia can be managed with appropriate medical interventions. Early diagnosis and preventive medicine for Schizophrenia are therefore active areas of research.

Assessment/Diagnosis of Schizophrenia at an early stage is challenging. Prominent (and persistent) symptoms like delusion, disorganized speech, catatonic movements or paranoia only occur at later stages. Due to this there are increased chances of false positive (and sometimes false negative) assessments.

Current assessment/diagnostic methods for Schizophrenia include psychological screening tests and image mapping of the subject's brain. Psychological screening tests are cheap but they require an experienced practitioner for effective diagnosis of Schizophrenia and are thus dependent on the human intellect for diagnosis. Image mapping of the subject's brain through use of latest imaging technologies such as MRI are very expensive. Though this provides a better chance for visualization of the improper brain functioning, alone it is not yet considered to be the most efficient technique for screening of Schizophrenia.

Recent studies have identified neurological and biochemical based markers for distinguishing between healthy and schizophrenic subjects. Some of these techniques involve invasive procedures which can be emotionally traumatic, especially for subjects suffering from neurological disorders like Schizophrenia. Further, there is no (commercially) available screening method which uses these biochemical markers. Non acceptability of these methods can at least be partially attributed to the relative low prediction accuracies for most of these methods.

A few studies have also suggested the use of the human microbiome in diagnosis of Schizophrenia. However, no such studies could identify any microbiome based signals that could be used to distinguish between healthy subjects and Schizophrenia affected patients with sufficient accuracy.

SUMMARY

Embodiments of the present disclosure present technological improvements as solutions to one or more of the above-mentioned technical problems recognized by the inventors in conventional systems. For example, in one embodiment, a system for assessing the risk of schizophrenia in a person has been provided. The system comprises a sample collection module, a DNA extractor, a sequencer, a database creation module, one or more hardware processors and a memory. The sample collection module collects a microbiome sample from swab of the person for the assessment of the risk of schizophrenia, wherein the microbiome sample comprising microbial cells. The DNA extractor extracts DNA from the microbial cells. The sequencer sequences the extracted DNA to get sequenced metagenomic reads. The database creation module creates a database of sensory protein sequences of a plurality of organisms, wherein the database of sensory protein sequences comprises information pertaining to the sensory proteins of all fully sequenced bacterial genomes obtained from a plurality of public repositories. The memory in communication with the one or more hardware processors, wherein the one or more first hardware processors are configured to execute programmed instructions stored in the memory, to generate sensory protein abundance profiles of case-control samples obtained from publicly available data; apply a random forest classifier on the generated sensory proteins abundance profiles of case-control samples to generate a classification model; quantify the abundance of a sensory protein from the sequenced metagenomic reads using the database of sensory protein sequences; assess the risk of the person to be in the schizophrenia diseased state using the classification model and the quantified abundance of the sensory protein in the metagenomic sample of the person, wherein the assessment results in the categorization of the person either in a low risk or a high risk of schizophrenia diseased state based on a predefined criteria; and provide a therapeutic construct to the person depending on the risk of the schizophrenia.

In another aspect, a method for assessing the risk of schizophrenia in a person has been provided. Initially, a database of sensory protein sequences of a plurality of organisms is created, wherein the database of sensory protein sequences comprises information pertaining to the sensory proteins of all fully or partially sequenced bacterial genomes obtained from a plurality of public repositories. Further sensory protein abundance profiles of case-control samples obtained from publicly available data is generated. In the next step, a random forest classifier is applied on the generated sensory protein abundance profiles of case-control samples to generate a classification model. Further, a microbiome sample is collected from swab of the person for the assessment of the risk of schizophrenia, wherein the microbiome sample comprising microbial cells. Further, DNA is extracted from the microbial cells. The extracted DNA is then sequenced to get sequenced metagenomic reads. Further, the abundance of a sensory protein from the sequenced metagenomic reads is quantified using the database of sensory protein sequences. Further, the risk of the person to be in the schizophrenia diseased state is assessed using the classification model and the quantified abundance of the sensory protein in the metagenomic sample of the person, wherein the assessment results in the categorization of the person either in a low risk or a high risk of schizophrenia diseased state based on a predefined criteria. And finally, a therapeutic construct is provided to the person depending on the risk of the schizophrenia.

In yet another aspect, one or more non-transitory machine readable information storage mediums comprising one or more instructions which when executed by one or more hardware processors cause assessing the risk of schizophrenia in a person has been provided. Initially, a database of sensory protein sequences of a plurality of organisms is created, wherein the database of sensory protein sequences comprises information pertaining to the sensory proteins of all fully or partially sequenced bacterial genomes obtained from a plurality of public repositories. Further sensory protein abundance profiles of case-control samples obtained from publicly available data is generated. In the next step, a random forest classifier is applied on the generated sensory protein abundance profiles of case-control samples to generate a classification model. Further, a microbiome sample is collected from swab of the person for the assessment of the risk of schizophrenia, wherein the microbiome sample comprising microbial cells. Further, DNA is extracted from the microbial cells. The extracted DNA is then sequenced to get sequenced metagenomic reads. Further, the abundance of a sensory protein from the sequenced metagenomic reads is quantified using the database of sensory protein sequences. Further, the risk of the person to be in the schizophrenia diseased state is assessed using the classification model and the quantified abundance of the sensory protein in the metagenomic sample of the person, wherein the assessment results in the categorization of the person either in a low risk or a high risk of schizophrenia diseased state based on a predefined criteria. And finally, a therapeutic construct is provided to the person depending on the risk of the schizophrenia.

It is to be understood that both the foregoing general description and the following detailed description are exemplary and explanatory only and are not restrictive of the invention, as claimed.

BRIEF DESCRIPTION OF THE DRAWINGS

The embodiments herein will be better understood from the following detailed description with reference to the drawings, in which.

DETAILED DESCRIPTION OF EMBODIMENTS

Figure 1:
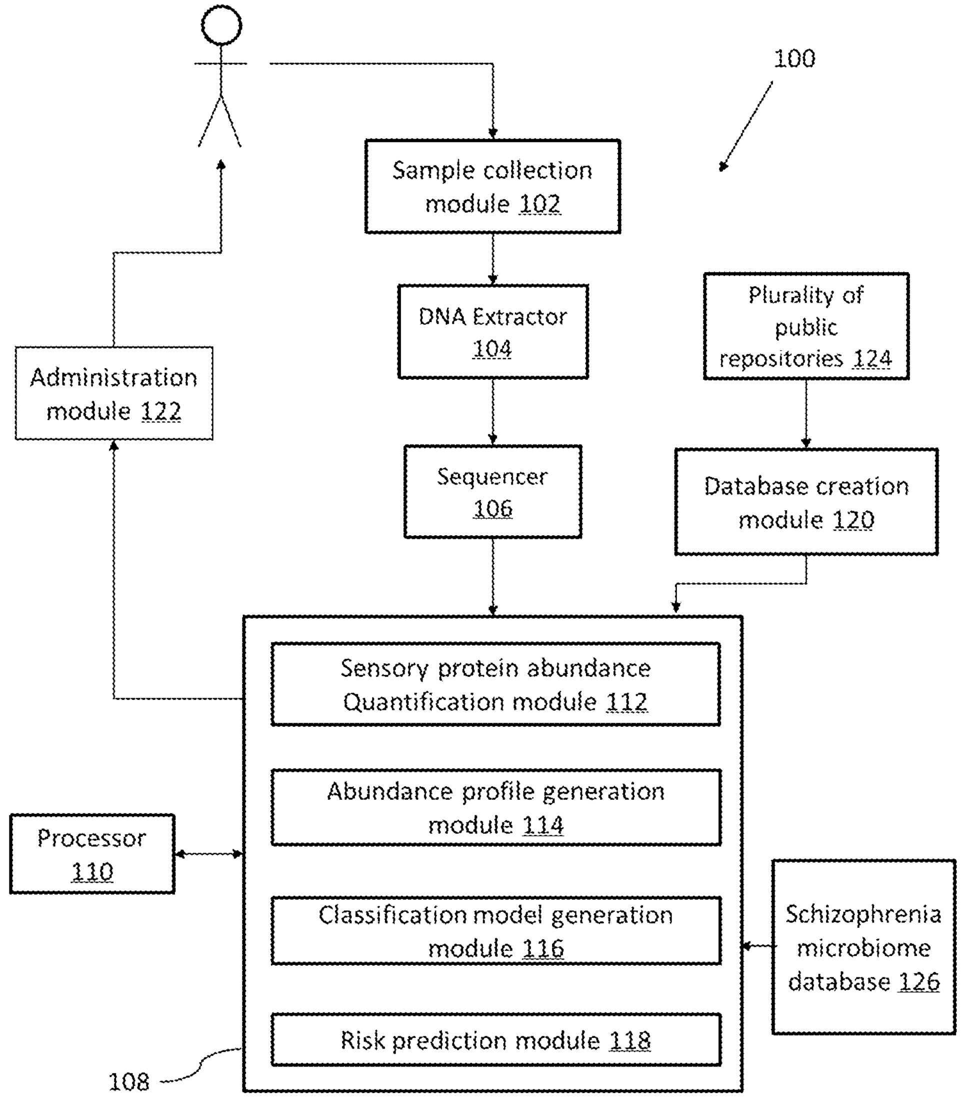
FIG. 1 illustrates a block diagram of a system for assessing the risk of Schizophrenia in a person according to an embodiment of the present disclosure.

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the scope of the disclosed embodiments. It is intended that the following detailed description be considered as exemplary only, with the true scope being indicated by the following claims.

Referring now to the drawings, and more particularly to FIG. 1 through FIG. 4B, where similar reference characters denote corresponding features consistently throughout the figures, there are shown preferred embodiments and these embodiments are described in the context of the following exemplary system and/or method.

According to an embodiment of the disclosure, a system 100 for assessing the risk of Schizophrenia in a person is presented in FIG. 1. The system 100 is configured to assess individuals to check the presence or absence of Schizophrenia, by quantifying the abundance of sensory proteins in their microbiome. The invention relates to a defined methodology that involves assessment and categorization of the person into healthy and schizophrenic based on the abundance of sensory proteins in the oropharyngeal microbiome. The systems and methods further describe microbiota based therapeutics for management of Schizophrenia through generating a therapeutic model and administering a consortium of healthy microbes which could modulate the disease microbiome composition towards a healthy equilibrium.

According to an embodiment of the disclosure, the system 100 comprises of a sample collection module 102, a DNA extractor 104, a sequencer 106, a memory 108 and a processor 110 as shown in FIG. 1. The processor 110 is in communication with the memory 108. The processor 110 is configured to execute a plurality of algorithms stored in the memory 108. The memory 108 further includes a plurality of modules for performing various functions. The memory 108 may include a sensory protein abundance quantification module 112, an abundance profile generation module 114, a classification model generation module 116 and a risk prediction module 118.

The system 100 also comprises a database creation module 120 created using a plurality of public repositories 124. The system 100 further comprises an administration module 122 as shown in the block diagram of FIG. 1. The system 100 also comprises a Schizophrenia microbiome database 126 as shown in the block diagram of FIG. 1.

According to an embodiment of the disclosure, the microbiome sample is collected using the sample collection module 102. The sample collection module 102 is configured to collect microbiome from swab such as oropharyngeal swab sample of the person, wherein 'microbiome' refers to the community of bacteria which resides in the oropharynx region of oral cavity. The microbiome sample in the form of saliva/stool/blood/other body fluids/swabs can also be collected from at least one body site/locations other than the oropharynx e.g. gut, skin, lung etc. The microbiome sample can also be collected from subjects of different geographies. The sample can also be collected from the person from one or multiple body sites at various stages before and after successful assessment of Schizophrenia. Moreover, the samples can also be collected from other mammals such as cow, dog, etc. The sample collection module 102 can include a variety of software and hardware interfaces, for example, a web interface, a graphical user interface, and the like and can facilitate multiple communications within a wide variety of networks N/W and protocol types, including wired networks, for example, LAN, cable, etc., and wireless networks, such as WLAN, cellular, or satellite.

The system 100 further comprises the DNA extractor 104 and the sequencer 106. DNA is first extracted from the microbial cells constituting the microbiome sample using laboratory standardized protocols by employing the DNA extractor 104. Next, sequencing is performed using the sequencer 106 to obtain the sequenced metagenomic reads. The sequencer 106 performs whole genome shotgun (WGS) sequencing from the extracted microbial DNA, using a sequencing platform after performing suitable pre-processing steps (such as, sheering of samples, centrifugation, DNA separation, DNA fragmentation, DNA extraction and amplification, etc.) The extracted and sequenced DNA sequences are then provided to the processor 110.

In another embodiment of the disclosure, the DNA extractor 104 and sequencer 106 are also configured to use universal primers to kinase domains to specifically pull down and amplify DNA sequences fragments encoding for sensory kinases. Other embodiments can also perform amplicon sequencing (such as, sequencing 16S rRNA gene, sequencing cpn60 gene, etc.) of the collected microbiome. Further, the DNA extractor 104 and the sequencer 106 are also configured to extract and sequence microbial transcriptomic (also referred to as meta-transcriptomic) data. The DNA extractor 104 and the sequencer 106 are also configured to perform any one of chip based hybridization, ELISA based separation, size/chargebased seclusion of specific class of DNA/RNA/protein and subsequently performs amplification and sequencing and/or quantification of the same. Sequencing may be performed using approaches which involve either a fragment library or a mate-pair library or a paired-end library or a combination of the same. Sequencing may also be performed using any other approaches such as by recording changes in the electric current while passing a DNA/RNA molecule through a nano-pore while applying a constant electric field or by using mass spectrometric techniques.

According to an embodiment of the disclosure, the system 100 comprises the database creation module 120. The database creation module 120 is configured to create a database of sensory protein sequences of all the organisms, wherein the database of sensory protein sequences comprises information pertaining to the proteins of all fully sequenced bacteria obtained from a plurality of public repositories 124. The plurality of public repositories may include, but not limited to NCBI, Protein Data Bank (PDB), UniProt, KEGG, Pfam, EggNOG, etc. Thus, the database creation is a onetime process. The pre-created database of sensory protein sequences can be used for the diagnosis of Schizophrenia as explained in the later part of the disclosure.

In another embodiment of the disclosure, the database of sensory proteins created using the database creation module 120 may also include sensory protein sequences from partially sequenced bacterial genomes and/or genomes of other microorganisms including but not restricted to viruses, fungi, micro-eukaryotes, etc.

According to an embodiment of the disclosure, the memory 108 comprises the sensory protein abundance quantification module 112. The sensory protein abundance quantification module 112 is configured to compute the abundance of the sensory protein encoding genes in the sequenced metagenomic reads using the database of sensory protein sequences. In an embodiment, following methodology can be used to compute the sensory protein abundance for the sequenced metagenomic reads.

Step 1: Perform a sequence alignment such as tBLASTN with the sequences in the created sensory protein sequence database as query against the sequenced metagenomic reads. The hits satisfying a minimum e-value threshold of $1.0{*}e^{-5}$ (0.00001) were considered as correct matches.

Step 2: For each bacterial strain in the sensory protein sequence database the cumulative of the matches of the sequenced metagenomic reads are computed to form the "Count of sensors" which indicates approximately the potential number of sensory protein coding regions in the genome for that particular bacterial strain for the microbiome sample from which the sequenced metagenomic reads were obtained. Also for each bacterial strain in the sensory protein sequence database the cumulative length of the nucleotide bases for all these hits is computed to form the "Covered base length" which indicates approximately the total length of the potential sensory protein coding regions in the genome for that particular bacterial strain for the microbiome sample from which the sequenced metagenomic reads were obtained.

Step 3: The calculation of the sensory protein abundance can be performed using two implementations: In the first implementation, computation of sensory protein abundance is performed by calculation of the ratio of the "Count of sensors" to the total size of the sequenced metagenomic reads constituting the microbiome sample, henceforth referred to as metagenomic size (in Megabases). This ratio indicates the cumulative number of sensory proteins for that bacterial strain coded per unit of the sequenced metagenomic reads constituting the microbiome sample. Thus, $$\text{Sensory Protein Abundance} = \frac{\text{Count of Sensors for a particular strain}}{\text{Metagenomic Size}}$$

In the second implementation, computation for the sensory protein abundance can be performed by calculation of the ratio of the "Covered base length" to the total metagenomic size (in Megabases) of the microbiome sample for each available bacterial strain. This ratio indicates the cumulative length of sensory protein coding regions (coding sequence) for that bacterial strain per unit of the sequenced metagenomic reads constituting the microbiome sample. Thus, $$\text{Sensory protein abundance} = \frac{\text{Covered base length for a particular strain}}{\text{Metagenomic Size}}$$

The sensory protein abundance for the sequenced metagenomic reads can also be computed using various other implementations of the process and are described as follows. In one implementation, the computation can be performed at any of the known taxonomic levels or the computation can also be performed at each of the different taxonomic levels using a mixture of organisms. The sensory protein abundance is initially computed for each available strain(s) and in one implementation can be cumulated to a desired taxonomic level. In other implementations, the computed sensory protein abundance may be replaced by any other statistical means, such as mean, median, mode, etc. Organisms other than bacteria (either alone or in combination with other taxonomic lineages) may also be employed. In yet another implementation, one or more group of proteins, other than sensory proteins may be used, either alone or in combination with the sensory proteins and/or taxonomic classifications.

According to an embodiment of the disclosure, the memory 108 also comprises the abundance profile generation module 114, the classification model generation module 116 and the risk prediction module 118. The abundance profile generation module 114 is configured to generating sensory protein abundance profiles from sequenced metagenomic reads obtained from publicly available data. The set of sequenced metagenomic reads can be used for training and/or testing. The abundance profiles of the sequenced metagenomic reads is used as the training and/or testing data for the generation of a model and testing its efficiency.

The classification model generation module 116 is configured to apply a random forest (RF) classifier on the abundance profiles of the subset of sequenced metagenomic reads to generate a classification model and test prediction accuracy on the other subset. In one embodiment, the microbiome samples, constituting of sequenced microbiome reads may be obtained from publicly available Schizophrenia microbiome data through Schizophrenia microbiome database 126. The microbiome samples, from which the sequenced metagenomic reads are obtained, are divided in a random set of 90% as the training set and rest of the 10% as the testing set. Thus, the generated classification model can also be used to classify the testing set as well.

The risk prediction module 118 is configured to assess the presence of Schizophrenia from the microbiome of the person providing oropharyngeal microbiome sample for risk assessment using the classification model, wherein the assessment results in the categorization of the person either in a low risk or a high risk of Schizophrenia based on predefined criteria. The machine learning technique of RF classifier was used for model based prediction using train and test set.

Figure 3:
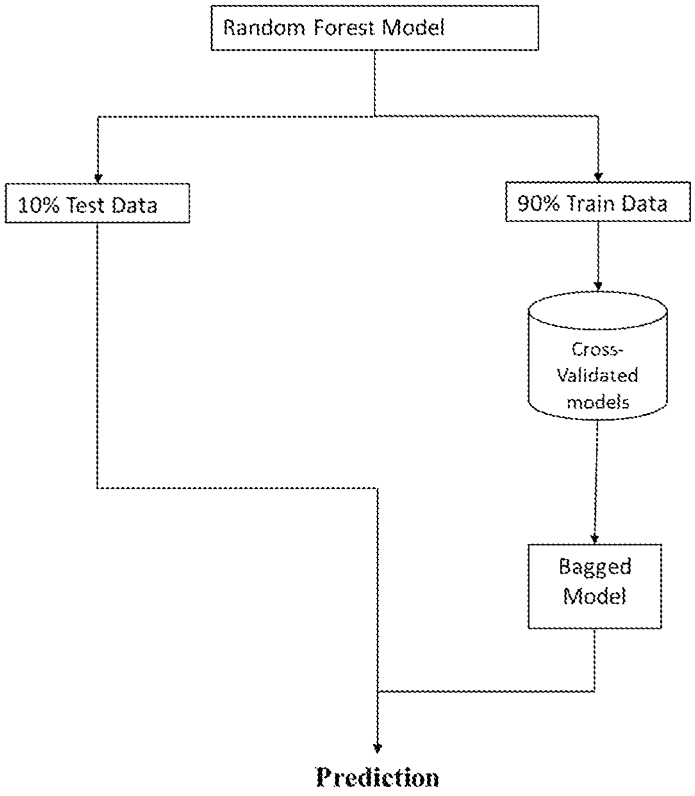
FIG. 3 shows a block diagram for generating a classification model to be used in the system of FIG. 1 according to an embodiment of the disclosure.

The classification model generation module 116 further creates a binary classification model as shown in FIG. 3. The binary classification model computes the risk of Schizophrenia using the machine learning technique of model based prediction by means of the Random Forest algorithm. Random forest approach (R 3.0.2, random Forest 4.6-7 package) was applied on the sensory protein abundance profiles of case-control sequenced microbiome reads which constituted the microbiome samples. A random set of 90% of the sequenced microbiome reads which constituted the microbiome samples were selected as the training set and rest of the 10% were considered as the test set.

The current implementation was computed using species level sensory protein abundance. The alternate implementations are:

- Using Abundance values of Sensory proteins (or any other group of proteins) at other taxonomic levels
- Using the Sensory (or any other group of proteins) count instead of covered base length
- Using any other model based prediction algorithm According to an embodiment of the disclosure, the system 100 also comprises of the administration module 122. The administration module 122 is configured to provide/administer a therapeutic construct to the person depending on the risk of the Schizophrenia. It should be appreciated that any of the well-known technique can be used to administer the construct. The administration module 122 uses at least one of a consortium/construct of healthy microbes, antibiotic drugs and pre/pro-/syn-/post-biotics and fecal microbiome transplant that would help the patient's gut microbiome to attain a healthy equilibrium without any adverse health effects.

The current treatment regime for Schizophrenia involves psychotherapy as well as use of strong antipsychotic drugs. The therapy may be provided in the form of any one (or a combination) of the known routes of administrations like intravenous solution, sprays, patches, band aids, pills, syrup, mouth wash, breath fresheners, chewing gums, etc. The therapeutics is suggested as a consortium of microbes based on their (inverse) correlation with the disease microbiome which can contribute to the therapeutic treatment for Schizophrenia by modulating the disease microbiome towards healthy equilibrium. Different implementations to identify the suitable therapeutic candidates are as following:

- The sub-set of the reported screening markers abundant in healthy subjects, i.e. Healthy Therapeutic Markers (HTMs) which have been previously identified in research to be non-pathogenic
- The different species and strains belonging to the same genus of the HTMs which have been previously identified in research to be non-pathogenic
- All organisms having >90% identity and coverage over the genome of HTMs and which have been previously identified in research to be non-pathogenic
- Any previously reported organisms which are known to boost the population of (non-pathogenic) HTMs and which have been previously identified in research to be non-toxic and do not cause any adverse effect
- One or more of a natural or synthetically derived compounds which boost the population of (non-pathogenic) HTMs, wherein the natural or synthetically derived compounds are non-toxic
- Any organism with identical sensory protein/kinase domain to HTMs and previously identified in research to be non-pathogenic/non-toxic
- one or more of a natural or synthetically derived compounds which targets the reported screening markers abundant in diseased subjects, i.e. Disease Markers (DMs), wherein the natural or synthetically derived compounds are non-toxic and do not cause any adverse effect
- Any organism previously reported, or any of its related similar organisms (similar through genomic make up or characteristic functions) which inhibit growth of reported screening markers abundant in diseased patients, i.e. Disease markers (DMs) and previously identified in research to be non-pathogenic.

Figure 2:
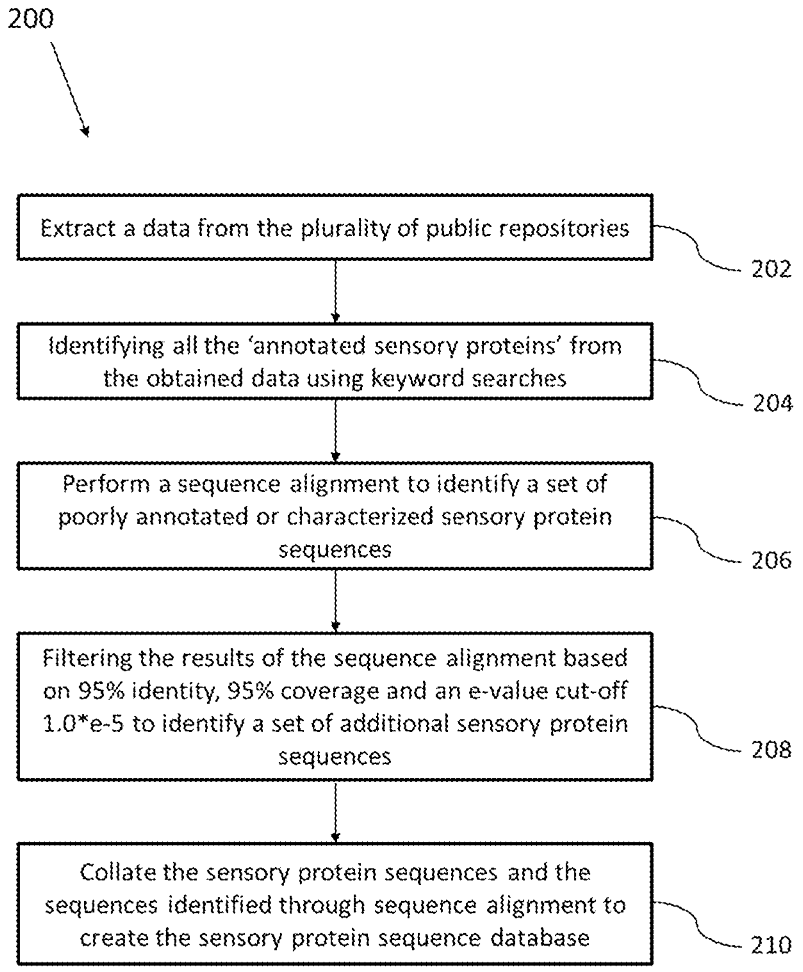
FIG. 2 shows a flowchart for creating a database of sensory protein abundances according to an embodiment of the disclosure.

A flowchart 200 for creating a database of sensory protein sequence is shown in FIG. 2. Initially at step 202, a data is extracted from the plurality of public repositories 124. In the next step 204, all the 'annotated sensory proteins' from the obtained data were identified using keyword searches. At step 206, followed by a sequence alignment step (BLAST) to identify the poorly annotated/less characterized sensory protein sequences. For the purpose, the sequences corresponding to the 'annotated sensory proteins' were used as the database and the rest of the obtained bacterial protein sequences were used as query. At step 208, the results of the sequence alignment is filtered based on 95% identity, 95% coverage and an e-value cut-off $1.0*e^{-5}$ (0.00001) to identify a set of additional sensory protein sequences;

And finally at step 210, the sensory protein sequences (those used as a database for the BLAST search) and the ones identified through BLAST analysis were collated into the sensory protein sequence database. In another embodiment, the database creation module 120 is also configured to create the database of interactome proteins and create a database of any other types of protein group/functional class.

In another embodiment of the disclosure, the sequence alignment may be performed using other techniques such as BLAT, DIAMOND, RAPSearch, BWA, Bowtie or through the use of clustering algorithms like BLASTCLUST, CLUSTALW, VSEARCH or any other heuristic techniques of identifying sequence/motif similarity.

Figure 4A:
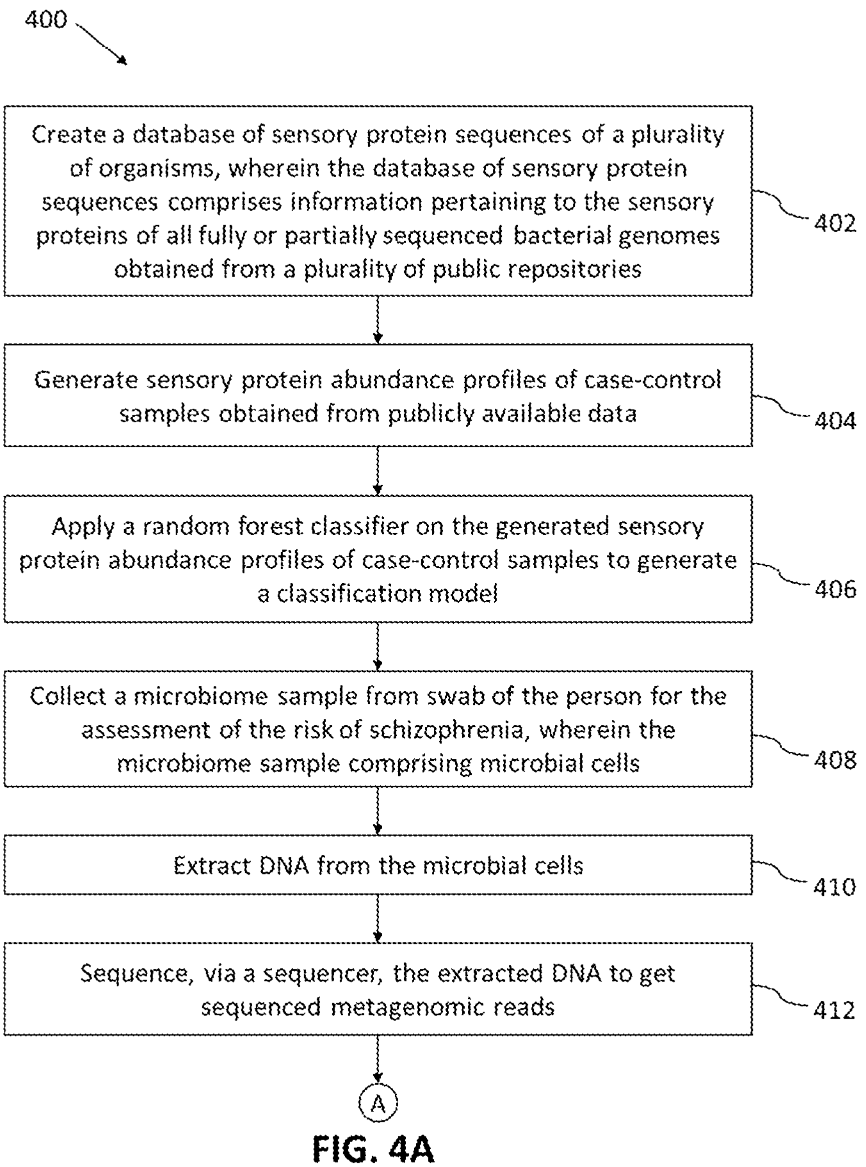
FIG. 4A-4B is a flowchart illustrating the steps involved in assessing the risk of Schizophrenia in the person according to an embodiment of the present disclosure.
Figure 4B:
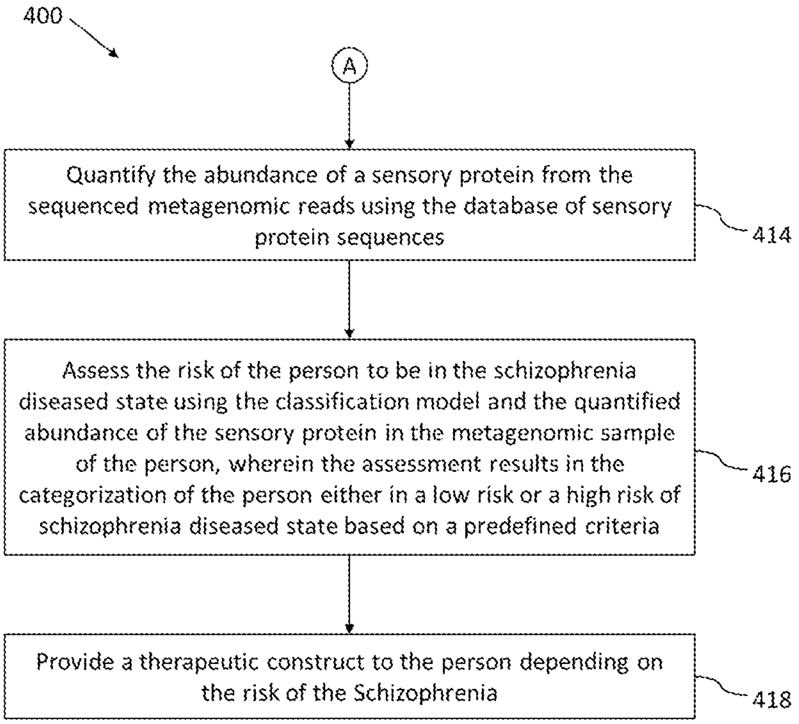

In operation, a flowchart 400 illustrating the steps involved for assessing the risk of Schizophrenia is shown in flowchart of FIG. 4A-4B. Initially at 402, a database of sensory protein sequences of a plurality of organisms is created, wherein the database of sensory protein sequences comprises information pertaining to the proteins of all fully sequenced bacteria obtained from a plurality of public repositories. The database of sensory protein sequences created through database creation module 120 comprises information pertaining to the proteins of all fully or partially sequenced bacteria obtained from a plurality of public repositories 124. It may be appreciated that the database creation is a one-time process and created before the test sample from a person/patient is provided for the diagnosis and thereafter therapeutic purposes. Further at step 404, the sensory protein abundance profiles of case-control samples obtained from publicly available data is generated. At step 406, a random forest classifier is applied on the generated sensory protein abundance profiles of case-control samples to generate a classification model using the classification model generation module 116. It may be appreciated that this generation of the classification model is a one-time process and created before the test sample from a person/patient is provided for the diagnosis and thereafter therapeutic purposes.

In the next step 408, a microbiome sample from swab such as oropharyngeal swab of the person is collected for the assessment of the risk of schizophrenia, wherein the microbiome sample comprising microbial cells. Later at step 410, DNA is extracted from the microbial cells using DNA extractor module 104. At step 412, the extracted DNA is sequenced via the sequencer 106, to get sequenced metagenomic reads. In the next step 414, the abundance of a sensory protein is quantified from the sequenced metagenomic reads using the database of sensory protein sequences. At step 416, the risk of the person to be in the schizophrenia diseased state is assessed using the classification model and the quantified abundance of the sensory protein in the metagenomic sample of the person, wherein the assessment results in the categorization of the person either in a low risk or a high risk of schizophrenia diseased state based on a predefined criteria. And finally at step 418, a therapeutic construct is provided to the person depending on the risk of the schizophrenia.

According to an embodiment of the disclosure, the system 100 for assessing and treating Schizophrenia in the person can also be explained with the help of following example. Publicly available oropharyngeal microbiome data, comprising of sequenced metagenomic reads from oropharyngeal swab microbiome samples, obtained from a previously published study was used for this evaluation. The sequenced metagenomic reads obtained from 32 metagenomic shotgun-sequenced oropharyngeal microbiome samples were used in the current evaluation and analysis.

A pairwise alignment using tBLASTN was performed using the derived Sensory Protein Sequence Database as query against the sequenced metagenomic reads. The protein-nucleotide translated BLAST or tBLASTN performs a comparison of a protein type query against all 6-frame translations of a nucleotide database. The blast hits satisfying the e-value threshold of $1.0^*e^{-5}$ (0.00001) were used to calculate the Sensory Protein Abundance across all bacterial strains, which constituted the sensory protein sequence database. For the current implementation the Sensory Protein Abundance were calculated at species level. Sensory Protein Abundance was computed by cumulating the abundance of sensory proteins for all the bacterial strains, constituting the sensory protein sequence database, of a particular species for each of the oropharyngeal microbiome samples. It was also computed by calculating median of the abundance of sensory proteins for all the bacterial strains, constituting the sensory protein sequence database, of a particular species for each of the oropharyngeal microbiome samples.

State of the art machine learning technique was implemented for model based prediction of the samples. Random Forest (RF) approach (R 3.0.2, random Forest 4.6-7 package) was applied and a random set of sequenced metagenomic reads comprising 90% of the microbiome samples were selected as the training set and rest of the 10% were considered as the test set. Subsequently 10 replicates on 10-fold cross-validation were performed on the train dataset to build 100 cross-validation RF models. The 'importance' of each of the features included in the cross-validation models was captured in form of GINI index. 'X' most 'important' features (here X was equal to 10), based on GINI index values were selected from each of the 100 models (in alternate implementations, X may vary from 2 to 'N', wherein 'N' is the total number of features). Each feature in the sub-set of features, that was obtained by choosing the 'X' most 'important' features from each of the 100 cross-validation RF models, was subsequently ranked on the basis of the sum of their GINI index values (in alternate implementation, the features may be ranked on the basis of their occurrence frequency in the sub-set of features). Next, multiple 'evaluation' models were obtained by cumulatively adding the next ranked feature in the feature sub-set with the features of the previous 'evaluation' model, wherein the first 'evaluation' model comprised of the top two features in the feature sub-set. Subsequently, the performance of all the 'evaluation' models were assessed on the basis of their performance and the best performing 'evaluation' model was chosen as the final 'bagged' model. The performance of the 'evaluation' models was evaluated on the basis of Balancing Score, followed by Mathews Correlation Coefficient (MCC) score and area under the curve (AUC) score. In cases where multiple models demonstrated identical performance measures, the 'evaluation' model with least number of features was chosen as the final 'bagged' model. The balancing score was computed as following.

$$\text{Balancing Score}=(\text{sensitivity}+\text{specificity})-\text{absolute}(\text{sensitivity}-\text{specificity})$$

The final 'bagged' model was then validated on the test set containing rest 10% of the dataset earlier kept aside as the independent test set. The accuracy of training model and the confidence probability of the binary prediction to be 'case' or 'control' (schizophrenic or healthy) were accounted. Table I below shows the cross-validation results of the study: Cross-Validation Results

TABLE I

| Classification | Train | | Test | |
|---|---|---|---|---|
| Basis | Sensitivity | Specificity | Sensitivity | Specificity |
| Taxonomy (Genus) | 85.71 | 78.57 | 50.00 | 50.00 |
| Taxonomy (Species) | 92.86 | 89.29 | 50.00 | 100.00 |
| Sensory Proteins (cumulated) | 92.86 | 92.86 | 100.00 | 100.00 |
| Sensory Proteins (median) | 92.86 | 92.86 | 100.00 | 100.00 |
| Kinase proteins* | 100.00 | 92.86 | 100.00 | 100.00 |

*Refer to results obtained using an alternate implementation wherein a subset of proteins (those containing a kinase domain) in the sensory protein database is used as the backend database. Using this subset of proteins allow for preparing a test kit and a Schizophrenia screening protocol that is highly economical and can be easily deployed for mass screening Table II below shows the list of discriminating taxa when abundance cumulated at species level (based on Sensory protein Abundance):

TABLE II

| Taxonomy | Healthy | Schizophrenic |
|---|---|---|
| *Acidithiobacillus caldus* | 0.560 | 0.105 |
| *Desulfovibrio aespoeensis* | 0.635 | 0.110 |
| *Desulfovibrio desulfuricans* | 0.702 | 0.132 |
| *Desulfurivibrio alkaliphilus* | 0.627 | 0.114 |
| *Halobacterium salinarum* | 0.008 | 0 |
| *Halobacterium sp.* | 0.008 | 0 |
| *Truepera radiovictrix* | 0.018 | 0 |

Table III below shows the list of discriminating taxa when median of abundance calculated at species level (based on Sensory protein Abundance):

TABLE III

| Taxonomy | Healthy | Schizophrenic |
|---|---|---|
| *Acidithiobacillus caldus* | 0.56 | 0.105 |
| *Desulfovibrio aespoeensis* | 0.635 | 0.11 |
| *Desulfurivibrio alkaliphilus* | 0.625 | 0.115 |
| *Halobacterium sp.* | 0.01 | 0 |
| *Jannaschia sp.* | 0.305 | 0.05 |

Based on the above results, one or more of the non-pathogenic HTMs, viz, *Acidithiobacillus caldus, Desulfovibrio aespoeensis, Desulfurivibrio alkaliphilus, Halobacterium salinarum, Halobacterium* sp., *Jannaschia* sp, *Truepera radiovictrix* or other non-pathogenic organisms satisfying one or more of the above criteria may be administered either alone or in concoction for therapeutic purposes. Further, one or more of the DMs may be targeted using antibiotics.

Thus, the Random forest model based prediction method applied can efficiently perform in risk assessment of Schizophrenia, based on sensory protein abundance from the oropharyngeal microbiome sample. The sensory protein abundance is clearly a potential biomarker for prediction of diseased state and can be similarly employed for diagnostic purposes in case of other diseases and disorders. The disclosure provides a non-invasive and cost effective method as compared to the existing methods. The embodiments of present disclosure herein provides a method and system for assessing and treating Schizophrenia in the person.

The written description describes the subject matter herein to enable any person skilled in the art to make and use the embodiments. The scope of the subject matter embodiments is defined by the claims and may include other modifications that occur to those skilled in the art. Such other modifications are intended to be within the scope of the claims if they have similar elements that do not differ from the literal language of the claims or if they include equivalent elements with insubstantial differences from the literal language of the claims.

The embodiments of present disclosure herein addresses unresolved problem of early assessment of Schizophrenia in the person. The embodiment provides a system and method to assess the risk of Schizophrenia in a person. Further depending on the risk, the therapeutic construct is also provided.

It is to be understood that the scope of the protection is extended to such a program and in addition to a computer-readable means having a message therein; such computer-readable storage means contain program-code means for implementation of one or more steps of the method, when the program runs on a server or mobile device or any suitable programmable device. The hardware device can be any kind of device which can be programmed including e.g. any kind of computer like a server or a personal computer, or the like, or any combination thereof. The device may also include means which could be e.g. hardware means like e.g. an application-specific integrated circuit (ASIC), a field-programmable gate array (FPGA), or a combination of hardware and software means, e.g. an ASIC and an FPGA, or at least one microprocessor and at least one memory with software processing components located therein. Thus, the means can include both hardware means and software means. The method embodiments described herein could be implemented in hardware and software. The device may also include software means. Alternatively, the embodiments may be implemented on different hardware devices, e.g. using a plurality of CPUs.

The embodiments herein can comprise hardware and software elements. The embodiments that are implemented in software include but are not limited to, firmware, resident software, microcode, etc. The functions performed by various components described herein may be implemented in other components or combinations of other components. For the purposes of this description, a computer-usable or computer readable medium can be any apparatus that can comprise, store, communicate, propagate, or transport the program for use by or in connection with the instruction execution system, apparatus, or device.

The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope of the disclosed embodiments. Also, the words “comprising,” “having,” “containing,” and “including,” and other similar forms are intended to be equivalent in meaning and be open ended in that an item or items following any one of these words is not meant to be an exhaustive listing of such item or items, or meant to be limited to only the listed item or items. It must also be noted that as used herein and in the appended claims, the singular forms “a,” “an,” and “the” include plural references unless the context clearly dictates otherwise.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., be non-transitory. Examples include random access memory (RAM), read-only memory (ROM), volatile memory, nonvolatile memory, hard drives, CD ROMs, DVDs, flash drives, disks, and any other known physical storage media.

It is intended that the disclosure and examples be considered as exemplary only, with a true scope of disclosed embodiments being indicated by the following claims.

What is claimed is:

1. A method for assessing a risk of schizophrenia in a person, the method comprising:

creating, via one or more hardware processors, a database of sensory protein sequences of a plurality of organisms, wherein the database of sensory protein sequences comprises information pertaining to the sensory proteins of all fully or partially sequenced bacterial genomes obtained from a plurality of public repositories, wherein the creation of the database of sensory protein sequences is a one-time process and created before a test microbiome sample from the person is provided for diagnosis and therapeutic purposes;

generating, via the one or more hardware processors, sensory protein abundance profiles of case-control samples obtained from publicly available data;

applying, via the one or more hardware processors, a random forest classifier on the generated sensory protein abundance profiles of case-control samples to generate a classification model, wherein the classification model generation comprises:

applying a Random Forest (RF) approach on the sensory protein abundance profiles of case-control samples, selecting a random set of sequenced metagenomic reads comprising 90% of microbiome samples as a training set and a remaining 10% as a test set, performing 10 replicates on 10-fold cross-validation on the training set to build 100 cross-validation RF models, capturing an importance of each feature included in the cross-validation RF models in terms of a GINI index value, selecting a predefined number of most important features based on GINI index values from each of the 100 cross-validation RF models to obtain a feature sub-set, ranking each of the features in the feature sub-set, on the basis of the sum of their GINI index values, obtaining multiple evaluation models by cumulatively adding a next ranked feature in the feature sub-set with features of a previous evaluation model, wherein a first evaluation model is comprised of the top two features in the feature sub-set, assessing a performance of all the evaluation models on the basis of their added features, evaluating the performance of all the evaluation models on the basis of a balancing Score, followed by Matthews correlation coefficient (MCC) and Area under the curve (AUC) scores, and the evaluation model with least number of features is chosen as a final classification model, and validating the final classification model on the test set containing the remaining 10% of the dataset earlier kept aside as the test set, wherein a confidence probability of a binary prediction to be case or control (schizophrenic or healthy) was accounted;

collecting a microbiome sample from a swab of the person for the assessment of the risk of schizophrenia, wherein the microbiome sample of the person comprises microbial cells;

extracting DNA from the microbial cells;

sequencing, via a sequencer, using the extracted DNA to get sequenced metagenomic reads;

quantifying, via the one or more hardware processors, the abundance of a sensory protein from the sequenced metagenomic reads using the database of sensory protein sequences;

assessing, via the one or more hardware processors, the risk of the person to be in a schizophrenia diseased state using the classification model and the quantified abundance of the sensory protein from the sequenced metagenomic reads of the person, wherein the person has the risk; and administering a therapeutic construct to the person with the risk of the schizophrenia, wherein the therapeutic construct comprises one or more non-pathogenic Healthy Therapeutic Markers (HTMs) abundant in a healthy population, a plurality of antibiotic drugs targeted against Disease Markers (DMs), prebiotics, probiotics, synbiotics, postbiotics and a fecal microbiome transplant to help the person's gut microbiome to attain a healthy equilibrium, wherein the one or more non-pathogenic HTMs comprises one or more of *Acidithiobacillus caldus, Desulfovibrio aespoeensis, Desulfurivibrio alkaliphilus, Halobacterium salinarum, Halobacterium* sp., *Jannaschia* sp, and *Truepera radiovictrix,* wherein the method is implemented for assessing and treating the schizophrenia in the person by modulating a disease microbiome towards the healthy equilibrium.

2. The method according to claim 1, wherein the therapeutic construct comprises one or more of:

a plurality of HTMs, wherein the plurality of Healthy Therapeutic Markers is non-pathogenic, species and strains belonging to a same genus of the HTMs, wherein the species and strains are non-pathogenic, a plurality of organisms having more than 90 percent identity and coverage over genomes of the HTMs, wherein the plurality of organisms are non-pathogenic, one or more organisms which boost a population of HTMs, wherein the one or more organisms are non-pathogenic, one or more of natural or synthetically derived compounds which boost the population of HTMs, wherein the one or more natural or synthetically derived compounds are non-toxic, or one or more of natural or synthetically derived compounds which targets the Disease Markers (DMs) and are non-toxic and do not cause any adverse effect.

3. The method according to claim 1, further comprising creating the database of sensory protein sequences as follows:

extracting data from the plurality of public repositories;

identifying all annotated sensory proteins from the extracted data using a set of keyword searches;

performing a sequence alignment to identify a set of poorly annotated or characterized sensory protein sequences, wherein the sequence alignment is performed using one or more of Basic Local Alignment Search Tool (BLAST), BLAST-like alignment tool (BLAT), DIAMOND alignment tool, RAPSearch tool, Burrows-Wheeler Aligner (BWA), Bowtie or through the use of clustering algorithms comprising BLASTCLUST, CLUSTALW, VSEARCH or heuristic techniques of identifying sequence similarity;

filtering the results of the sequence alignment based on 95% identity, 95% coverage and an e-value cut-off 0.00001 to identify a set of additional sensory protein sequences; and collating the sensory protein sequences and the sequences identified through sequence alignment to create the sensory protein sequence database.

4. The method according to claim 1, wherein the plurality of public repositories comprises one or more of NCBI database, Protein Data Bank, KEGG database, Pfam database or EggNOG.

5. The method according to claim 1, wherein quantifying the abundance of the sensory protein from the sequenced metagenomic reads using the database of sensory protein sequences comprises:

performing a sequence alignment with the sequences in the created sensory protein sequence database as queries against the sequenced metagenomic reads, wherein hits satisfying a minimum e-value threshold of 0.00001 are considered as correct matches;

computing cumulative matches of the sequenced metagenomic reads to form a count of sensors for each bacterial strain in the sensory protein sequence database, wherein the count of sensors indicates approximately a potential number of sensory protein coding regions in the genome for a particular bacterial strain for the microbiome sample from which the sequenced metagenomic reads were obtained;

computing a cumulative length of nucleotide bases for all hits for each bacterial strain in the sensory protein sequence database to form a covered base length, wherein the covered base length indicates approximately the total length of the potential sensory protein coding regions in the genome for that particular bacterial strain for the microbiome sample from which the sequenced metagenomic reads were obtained;

quantifying the sensory protein abundance using one of the following:

calculating a ratio of the count of sensors to a total metagenomic size (in Megabases) wherein total metagenomic size (in Megabases) is the size of the sequenced metagenomic reads constituting the microbiome sample, or calculating the ratio of the covered base length of the particular strain to the total metagenomic size (in Megabases) of the microbiome sample for each available bacterial strain.

* * * * *